(12) United States Patent
Truong et al.

(10) Patent No.: US 8,570,649 B2
(45) Date of Patent: Oct. 29, 2013

(54) DUAL-MODE RASTER POINT SCANNING/LIGHT SHEET ILLUMINATION MICROSCOPE

(75) Inventors: Thai V. Truong, Pasadena, CA (US); John M. Choi, Tujunga, CA (US); Scott E. Fraser, LaCanada, CA (US); Willy Supatto, Paris (FR); David S. Koos, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 274 days.

(21) Appl. No.: 12/916,124

(22) Filed: Oct. 29, 2010

(65) Prior Publication Data

US 2011/0134521 A1   Jun. 9, 2011

Related U.S. Application Data

(60) Provisional application No. 61/256,010, filed on Oct. 29, 2009, provisional application No. 61/256,005, filed on Oct. 29, 2009.

(51) Int. Cl.
*G02B 21/06* (2006.01)
*G02B 21/00* (2006.01)

(52) U.S. Cl.
USPC .......................... 359/385; 359/368

(58) Field of Classification Search
USPC .................... 359/388, 389, 368, 385
See application file for complete search history.

(56) References Cited

U.S. PATENT DOCUMENTS

| | | |
|---|---|---|
| 6,020,591 A | 2/2000 | Harter et al. |
| 6,844,963 B2 | 1/2005 | Iketaki et al. |
| 7,787,179 B2 | 8/2010 | Lippert et al. |
| 2007/0087284 A1 | 4/2007 | Fleming et al. |
| 2007/0109633 A1 | 5/2007 | Stelzer |
| 2007/0148760 A1 | 6/2007 | Klesel et al. |
| 2008/0043786 A1* | 2/2008 | Wilhelm et al. ............... 372/20 |
| 2008/0116392 A1 | 5/2008 | Brooker |
| 2009/0027769 A1* | 1/2009 | Saito et al. .................. 359/385 |
| 2009/0028503 A1* | 1/2009 | Garrett et al. ................. 385/18 |
| 2009/0225413 A1* | 9/2009 | Stelzer et al. ............... 359/385 |

(Continued)

FOREIGN PATENT DOCUMENTS

| | | | |
|---|---|---|---|
| DE | 102007047461.1 | * | 4/2009 |
| EP | 1207387 A1 | | 5/2002 |

(Continued)

OTHER PUBLICATIONS

Huisken et al., "Even Fluorescence Excitation by Multidirectional Selective Plane Illumination Microscopy." Sep. 1, 2007 Optics Letters vol. 32. pp. 2608-2610.*

(Continued)

*Primary Examiner* — Thomas K Pham
*Assistant Examiner* — William M Johnson
(74) *Attorney, Agent, or Firm* — KPPB LLP

(57) ABSTRACT

An apparatus for and method of performing light sheet microscopy (LISH) and light scanning microscopy (RAPS) in a single device are provided. The dual-mode imaging microscope allows for the use of both LISH and RAPS in a single instrument. This dual-mode device will allow researchers to have access to both types of microscopy, allowing access to the widest possible selection of samples. In addition, the device will reduce the high costs and space requirements associated with owning two different microscopes (LISH and RAPS).

27 Claims, 9 Drawing Sheets

(56) References Cited

U.S. PATENT DOCUMENTS

| | | | |
|---|---|---|---|
| 2010/0067102 A1 | 3/2010 | Yokoi et al. | |
| 2010/0075361 A1* | 3/2010 | Mattoussi et al. | 435/29 |
| 2010/0276608 A1* | 11/2010 | Liu et al. | 250/459.1 |
| 2010/0309548 A1* | 12/2010 | Power et al. | 359/385 |
| 2011/0115895 A1 | 5/2011 | Huisken | |
| 2011/0122488 A1 | 5/2011 | Truong et al. | |
| 2012/0141981 A1 | 6/2012 | Pantazis et al. | |

FOREIGN PATENT DOCUMENTS

| | | |
|---|---|---|
| WO | 9107651 | 5/1991 |
| WO | WO 2009043473 A1 * | 4/2009 |
| WO | 2011/059826 | 5/2011 |
| WO | 2011/059833 | 5/2011 |
| WO | 2011059826 | 5/2011 |
| WO | 2011059833 | 5/2011 |

OTHER PUBLICATIONS

Bewersdorf et al., "Multifocal multiphoton microscopy", Optics Letters, May 1, 1998, vol. 23, No. 9, pp. 655-657.

Bousso, "Real-time imaging of T-cell development", Current Opinion in Immunology, 2004, vol. 16, pp. 400-405.

Breuninger et al., "Lateral modulation boosts image quality in single plane illumination fluorescence microscopy", Optics Letters, Jun. 1, 2007, vol. 32, No. 13, pp. 1938-1940.

Campagnola et al., "Second-harmonic imaging microscopy for visualizing biomolecular arrays in cells, tissues and organisms", Nature Biotechnology, Nov. 2003, vol. 21, No. 11, pp. 1356-1360.

Denk et al., "Two-Photon Laser Scanning Fluorescence Microscopy", Reports, Apr. 6, 1990, vol. 248, No. 4951, pp. 73-76.

Dodt et al., "Ultramicroscopy: three-dimensional visualization of neuronal networks in the whole mouse brain", Nature Methods, Apr. 2007, vol. 4, No. 4, pp. 331-336.

Fahrbach et al., "Microscopy with self-reconstructing beams", Nature Photonics, Nov. 2010, vol. 4, pp. 780-785.

Friedl, "Immunological techniques Dynamic imaging of the immune system", Current Opinion in Immunology, 2004, vol. 16, pp. 389-393.

Fuchs et al., "Thin laser light sheet microscope for microbial oceanography", Optics Express, Jan. 28, 2002, vol. 10, No. 2, pp. 145-154.

Holekamp et al., "Fast Three-Dimensional Fluorescence Imaging of Activity in Neural Populations by Objective-Coupled Planar Illumination Microscopy", Neuron, Mar. 13, 2008, vol. 57, pp. 661-672.

Huisken et al., "Even fluorescent excitation by multidirectional selective plane illumination microscopy", Optics Letters, Sep. 1, 2007, vol. 32, No. 17, pp. 2608-2610.

Huisken et al., "Optical Sectioning Deep Inside Live Embryos by Selective Plane Illumination Microscopy", Science, 2004, vol. 305, pp. 1007-1009.

Huisken et al., "Selective plane illumination microscopy techniques in developmental biology", Development, 2009, vol. 136, pp. 1963-1975.

Ji et al., "Adaptive optics via pupil segmentation for high-resolution imaging in biological tissues", Nature Methods, Feb. 2010, vol. 7, No. 2, pp. 141-150.

Ji et al., "Advances in the speed and resolution of light microscopy", Current Opinion in Neurobiology, 2008, vol. 18, pp. 605-616.

Ji et al., "High-speed, low-photodamage nonlinear imaging using passive pulse splitters", Nature Methods, Feb. 2008, vol. 5, No. 2, pp. 197-202.

Keller et al., "Fast, high-contrast imaging of animal development with scanned light sheet-based structured-illumination microscopy", Nature Methods, Advance Online Publication, Jul. 4, 2010, pp. 1-9.

Keller et al., "Quantitative in vivo imaging of entire embryos with Digital Scanned Laser Light Sheet Fluorescence Microscopy", Current Opinion in Neurobiology, 2009, vol. 18, pp. 1-9.

Keller et al., "Reconstruction of Zebrafish Early Embryonic Development by Scanned Light Sheet Microscopy", Science, Nov. 14, 2008, vol. 322, pp. 1065-1069.

Kerr et al., "Imaging in vivo: watching the brain in action", Nature Review, Neuroscience, Mar. 2008, vol. 9, pp. 195-205.

Mavrakis et al., "Lighting up developmental mechanisms: how fluorescence imaging heralded a new era", Development, 2010, vol. 137, pp. 373-387.

McMahon et al., "Dynamic Analyses of *Drosophila* Gastrulation Provide Insights into Collective Migration", Science, Dec. 5, 2008, vol. 322, pp. 1546-1550.

Mertz, "Nonlinear microscopy: new techniques and applications", Current Opinion in Neurobiology, 2004, vol. 14, pp. 610-616.

Olivier et al., "Cell Lineage Reconstruction of Early Zebrafish Embryos Using Label-Free Nonlinear Microscopy", Science, Aug. 20, 2010, vol. 329, pp. 967-971.

Olivier et al., "Two-photon microscopy with simultaneous standard and extended depth of file using a tunable acoustic gradient-index lens", Optics Letters, Jun. 1, 2009, vol. 34, No. 11, pp. 1684-1686.

Palero et al., "A simple scanless two-photon fluorescence microscope using selective plane illumination", Optics Express, Apr. 12, 2010, vol. 18, No. 8, pp. 8491-8498.

Pantazis et al., "Second harmonic generating (SHG) nanoprobes for in vivo imaging", PNAS, Aug. 17, 2010, vol. 107, No. 33, pp. 14535-14540.

Preibisch et al., "Software for bead-based registration of selective plan illumination microscopy data", Nature Methods, Jun. 2010, vol. 7, No. 6, 20 pgs.

Provenzano et al., "Shining new light on 3D cell motility and the metastatic process", Trends in Cell Biology, 2009, vol. 19, No. 11, pp. 638-648.

Pu et al., "Nonlinear Optical Properties of Core-Shell Nanocavities for Enhanced Second-Harmonic Generation", Physical Review Letters, May 21, 2010, vol. 104, pp. 2074021-2074024.

Schonle et al., "Heating by absorption in the focus of an objective lens", Optics Letters, Mar. 1, 1998, vol. 23, No. 4, pp. 325-327.

Supatto et al., "Quantitative imaging of collective cell migration during *Drosophila* gastrulation: multiphoton microscopy and computational analysis", Nature Protocols, 2009, vol. 4, No. 10, pp. 1397-1412.

Vermot et al., "Fast fluorescence microscopy for imaging the dynamics of embryonic development", HFSP Journal, Jun. 2008, vol. 2, No. 3, pp. 143-155.

Verveer et al., "High-resolution three-dimensional imaging of large specimens with light sheet-based microscopy", Nature Methods, Apr. 2007, vol. 4, No. 4, pp. 311-313.

Voie et al., "Orthogonal-plan fluorescence optical sectioning: three-dimensional imaging of macroscopic biological specimens", Journal of Microscopy, Jun. 1993, vol. 170, Pt. 3, pp. 229-236.

Williams et al., "Interpreting Second-harmonic Generation Images of Collagen I Fibrils", Biophysical Journal, Feb. 2005, vol. 88, pp. 1377-1386.

Zipfel et al., "Nonlinear magic: multiphoton microscopy in the biosciences", Nature Biotechnology, Nov. 2003, vol. 21, No. 11, pp. 1369-1377.

Volodymyr et al., "SLM microscopy: scanless two-photon imaging and photostimulation with spatial light modulators, 2008, Frontiers in Neural Circuits", vol. 2, Article 5, pp. 1-14.

* cited by examiner

__US 8,570,649 B2__

DUAL-MODE RASTER POINT SCANNING/LIGHT SHEET ILLUMINATION MICROSCOPE

CROSS-REFERENCE TO RELATED APPLICATIONS

The current application claims priority to U.S. Provisional Application Nos. 61/256,005 and 61/256,010, both filed, Oct. 29, 2009, the disclosures of each of which are incorporated herein by reference.

STATEMENT OF FEDERAL FUNDING

The federal government has rights to current invention pursuant to a funding provided in accordance with grant numbers EY018241 and HG004071, issued by the National Institutes of Health, and grant number DB10852883, issued by the National Science Foundation.

FIELD OF THE INVENTION

The present invention relates generally to imaging microscopes and microscopy, and more specifically to a microscope that allows for the operation of the device in both light scanning and light sheet illumination modes.

BACKGROUND OF THE INVENTION

Advanced optical microscopy techniques offer unique opportunities to investigate biological processes in vivo. The ability to image tissues or organisms in three dimensions (3D) and/or over time (4D imaging) permits a wide range of applications in neuroscience, immunology, cancer research, and developmental biology. (See, e.g., Mertz, Curr. Opin. Neurobiol. 14, 610-616, (2004); Kerr, J. N. D. & Denk, W., Nature Reviews Neuroscience 9, 195-205, (2008); Friedl, P., Current Opinion in Immunology 16, 389-393, (2004); Bousso, P., Current Opinion in Immunology 16, 400-405, (2004); Provenzano, P. P., et al., Trends in Cell Biology 19, 638-648, (2009); Keller, P. J., et al., Science 322, 1065-1069 (2008); McMahon, A., et al., Science 322, 1546-1550 (2008); and Mavrakis, M., et al., Development 137, 373-387, (2010), the disclosures of each of which are incorporated herein by reference.) Fundamental light-matter interactions, such as light scattering, absorption, and photo-induced biological toxicity, set the limits on the performance parameters of various imaging technologies in terms of spatial resolution, acquisition speed, and depth penetration (how deep into a sample useful information can be collected). Often, maximizing performance in any one of these parameters necessarily means degrading performance in the others. (See, e.g., Ji, N., et al., Curr. Opin. Neurobiol. 18, 605-616, (2008) and Vermot, J., et al., HFSP Journal 2, 143-155 (2008), the disclosures of each of which are incorporated herein by reference.)

Such tradeoffs in performance are seen in comparing two current well-known 4D fluorescence imaging techniques of raster point scanning (RAPS) microscopy and light sheet (LISH) microscopy: RAPS excels in imaging of flat samples, while LISH excels in imaging of 3D samples and allows higher acquisition speed and lower phototoxicity. In RAPS microscopy, also known in the literature as laser scanning microscopy (LSM), the images are generated one voxel at a time by raster-scanning a tightly-focused laser spot through the sample, and 3D resolution is achieved by spatial-filtering of the emitted signal or by relying on nonlinear excitation to produce signal only at the focus spot (See, e.g., Pawley, Handbook of Confocal Microscopy, 3$^{rd}$ Edition, New York: Springer (2006), the disclosure of which is incorporated herein by reference.) The acquisition speed of RAPS is, however, limited since the image is collected one voxel at a time. Also, the phototoxicity quality of RAPS is relatively high due to the high laser light intensity concentrated at the focus spot.

LISH microscopy is a century-old technology that has seen much development and refinement in recent years, under names ranging from Orthogonal Plane Fluorescence Optical Sectioning (OPFOS), Thin Laser light Sheet Microscopy (TLSM), Selective Plane Illumination Microscopy (SPIM) (FIG. 1A, high-speed imaging of live zebrafish heart), Objective Coupled Planar Illumination (OCPI) (FIG. 1B, high-speed calcium imaging of neurons), ultramicroscopy (FIG. 1C, blood vessel system of mouse embryo), and Digital Scanned Laser Light Sheet Fluorescence Microscopy (DSLM) (FIG. 1D, in Coto imaging of developing zebrafish embryo), among others. (See, e.g., Siedentopf, H. & Zsigmondy, R., Ann. Phys.-Berlin 10, 1-39 (1902); Voie, A. H., et al., J. Microsc.-Oxf. 170, 229-236 (1993); Fuchs, E., et al., Opt. Express 10, 145-154 (2002); Huisken, J., et al., Science 305, 1007-1009 (2004); Holekamp, T. F., et al., Neuron 57, 661-672 (2008); Dodt, H. U. et al., Nat. Methods 4, 331-336 (2007); Huisken, J. & Stainier, D. Y. R., Development 136, 1963-1975 (2009); and Keller, P. J. & Stelzer, E. H. K., Curr. Opin. Neurobiol. 18, 624-632 (2009), the disclosures of each of which are incorporated herein by reference.)

In LISH, (FIG. 1E) a planar sheet of light is used to illuminate the sample, generating fluorescence signal over a thin optical section of the sample, which is then imaged from the direction orthogonal to the light sheet, with a wide-field imaging camera. Axial sectioning results from the thinness of the light sheet, while lateral resolution is determined by the detection optics. The orthogonal geometry between the illumination and detection pathways of LISH, compared to the collinear geometry of conventional microscopes, not only enables higher imaging speed due to the parallel image collection (millions of voxels can be imaged simultaneously), but also reduces phototoxicity because only a single focal plane of the sample is illuminated at a time, and because the laser light power is spread out in space over the extended sheet (as compared a single focus spot in the RAPS case). The low phototoxicity of LISH makes it the ideal choice for long-term time-lapsed imaging where a live biological sample is observed over an extended time window, from several hours to several days. LISH microscopy also allows imaging of a 3D sample from different views, thus facilitating improved coverage and resolution for samples such as a whole developing embryo. LISH, however, requires that the sample can be optically accessed from the side, which precludes samples that are flat.

Thus, it can be seen that the two imaging modalities of RAPS and LISH microscopy are complementary, each ideally suited for a particular type of samples. Ideally, a biomedical research laboratory would like to have access to both types of microscopy, allowing access to the widest possible selection of samples. However, there is a lack of commercially available LISH microscopes, and even if a commercial LISH microscope is available there is the high cost, both in monetary and space-related terms, associated with owning two different microscopes in order to do both LISH and RAPS microscopy.

Accordingly, it would be advantageous to develop an optical microscope that allows for the simultaneous performance of RAPS and LISH capable of providing new imaging capabilities heretofore unobtainable with conventional microscopy techniques.

SUMMARY OF THE INVENTION

The present invention is directed to a microscope device that may be operated in both raster point scanning and light sheet modes.

In one embodiment, the dual-mode imaging microscope includes the following components:
An excitation source capable of producing an excitation beam wherein the at least one excitation beam path is provided with a scanning optic capable of scanning said excitation beam in at least two dimensions;
a sample holder in optical communication with the excitation source such that a sample contained therein is excited by said excitation beam;
a light scanning microscope unit including:
   a light scanning microscope excitation optic capable of focusing the scanned excitation beam on the sample holder and scanning said excitation beam across said sample holder in a pre-determined path, and
   a light scanning microscope detector defining at least one light scanning detection focal plane and capable of detecting an excitation generated signal contrast from the sample holder, the light scanning microscope detector being disposed such that the axis of detection of the at least one light scanning detection focal plane is substantially collinear to the excitation beam;
a light sheet microscope unit including:
   a light sheet microscope excitation optic capable of laterally scanning the excitation beam along a desired axis of the excitation beam path to produce a substantially two-dimensional sample excitation region having an effectively uniform excitation intensity which extends in the direction of an excitation axis of the excitation beam path and transversely thereto and intersects with at least a portion of the sample holder, and
   a light sheet microscope detector defining at least one light sheet detection focal plane and capable of detecting an excitation generated signal contrast from the sample excitation region, the light sheet microscope detector being disposed such that the axis of detection of the at least one light sheet detection focal plane is substantially orthogonal to the sample excitation region; and
an optical relay disposed downstream of said scanning optics, the optical relay capable of being removably interposed into the excitation beam, such that the excitation beam may be directed either toward the light scanning microscope illumination optic or the light sheet microscope illumination optic.

In another embodiment of the microscope the optical relay is a periscope having a 4f optical configuration.

In still another embodiment of the microscope, the excitation source is a continuous-wave laser producing an excitation beam in the visible wavelength range, said excitation source being capable of inducing 1-photon-excited signal contrast for imaging, and wherein said signal contrast is proportional to $I^n$, where I is the instantaneous intensity of the excitation beam at the sample excitation region and n is the number of photons involved in the excitation, and where n is 1. In another such embodiment, the excitation source is capable of producing an excitation beam of high enough intensity to induce sufficient levels of multi-photon excitation to produce signal contrast for imaging, and n is greater than 1.

In yet another embodiment of the microscope, the excitation source is a pulsed near-infrared laser selected from the group consisting of lasers having pulse durations in the range of nanosecond, picoseconds, and femtosecond.

In sill yet another embodiment of the microscope, the detected signal contrast is selected from the group consisting of 1-photon-excited fluorescence, Rayleigh scattering, Raman-shifted scattering, second harmonic generation, third harmonic generation, sum frequency generation, and stimulated Raman scattering.

In still yet another embodiment of the microscope, the at least one excitation source is capable of creating two coaxial and oppositely aligned excitation beams, such that said sample excitation region is formed from the overlap of said two excitation beams.

In still yet another embodiment of the microscope, the numerical aperture of at least one of either the light scanning microscope excitation optic or the light sheet microscope excitation optic is adjustable. In one such embodiment, the adjustable numerical aperture comprises a beam expander with an adjustable expanding ratio.

In still yet another embodiment of the microscope, the numerical aperture of at least one of either the light scanning microscope excitation optic or the light sheet microscope excitation optic is anisotropic along at least two axes of said excitation beam.

In still yet another embodiment of the microscope, focal volume engineering is applied to the excitation beam to optimize for light sheet imaging. In one such embodiment, the focal volume engineering is implemented using one of the techniques selected from the group consisting of having the numerical aperture of the excitation focusing optics being anisotropic along at least two axes of said excitation beam, and having the excitation beam be a Bessel beam. In another such embodiment, the focal engineering is implemented by one or more optical elements selected from the group consisting of two orthogonally oriented sequential adjustable slit apertures, a plurality of independently expanding beam expanders, liquid crystal spatial light modulators, digital micromirror device spatial light modultators, and axiconic lens.

In still yet another embodiment of the microscope, the sample holder is moveable relative to the sample excitation region along or about at least one axis.

In still yet another embodiment of the microscope, the sample excitation region is moveable relative to the sample holder along or about at least one axis.

In still yet another embodiment of the microscope, the excitation beam is one of either substantially planar-shaped or linearly-shaped.

In still yet another embodiment of the microscope, the light sheet microscope unit incorporates a technique selected from the group consisting of Orthogonal Plane Fluorescence Optical Sectioning (OPFOS), Selective Plane Illumination Microscopy (SPIM), Ultramicroscopy, and Digital Scanned Laser Light Sheet Fluorescence Microscopy (DSLM).

The invention is also directed to a method of imaging an object using a dual-mode imaging microscope comprising the following:
   producing an excitation beam, and directing said excitation beam along an excitation beam path;
   scanning said excitation beam along a predetermined path;
   placing a sample within the optical path of said excitation beam to generate a signal contrast;
   directing said excitation beam into an optical relay capable of selecting between one of either a light scanning mode or a light sheet mode;

wherein in the light scanning mode the method further includes:
  focusing the excitation beam to a point scanning region and scanning said scanning region across the sample in a pre-determine path to produce a signal contrast in said sample, and
  detecting said signal contrast along a detection axis that is substantially collinear to the excitation beam; and
wherein in the light sheet mode the method further includes:
  focusing and laterally scanning said excitation beam along a desired axis of the excitation beam path to produce a substantially two-dimensional sample excitation region having an effectively uniform excitation intensity which extends in the direction of an excitation axis of the excitation beam path and transversely thereto and intersects with at least a portion of the sample holder, and
  detecting said signal contrast along a detection axis that is substantially orthogonal to the sample excitation region.

In another such embodiment of the method, the imaging is performed in one of either a 3D or 4D mode.

BRIEF DESCRIPTION OF THE DRAWINGS

These and other features and advantages of the present invention will be better understood by reference to the following detailed description when considered in conjunction with the accompanying drawings and data, wherein.

DETAILED DESCRIPTION OF THE INVENTION

The current invention is directed to a novel imaging microscope capable of operating in both raster point scanning (RAPS) and light sheet (LISH) modes. The microscope device uses a special optical arrangement that either allows for the simultaneous use of RAPS and LISH, or that allows for the conversion of a conventional RAPS microscope into a LISH microscope.

RAPS Microscopy

Figure 1A:
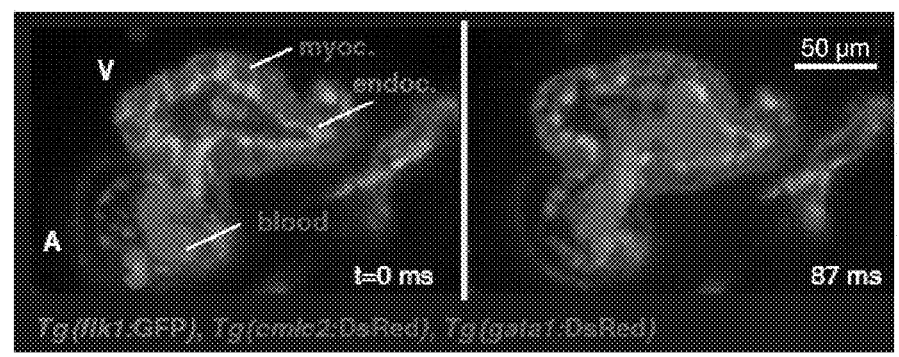
FIGS. 1A to 1D provide images and data form experiments taken using: (A) SPIM; (B) ultramicroscopy; (C) OCIP; and (D) DSLM.
Figure 1B:
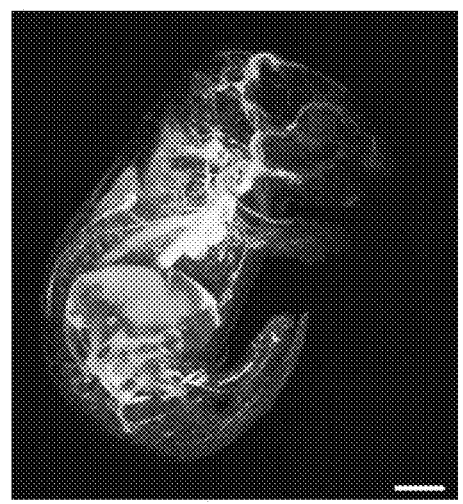
Figure 1C:
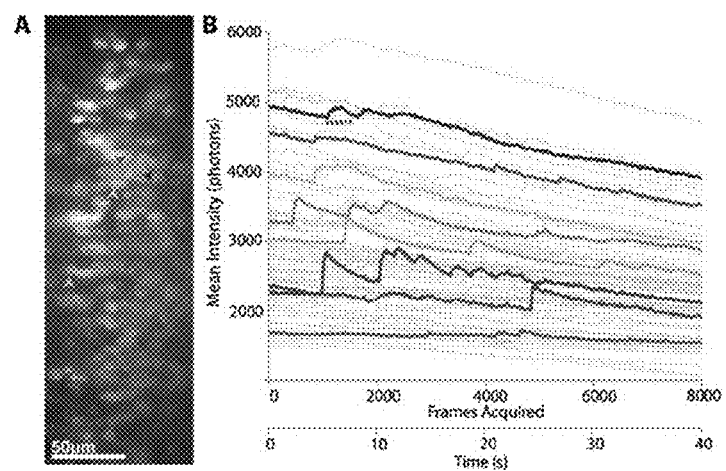
Figure 1D:
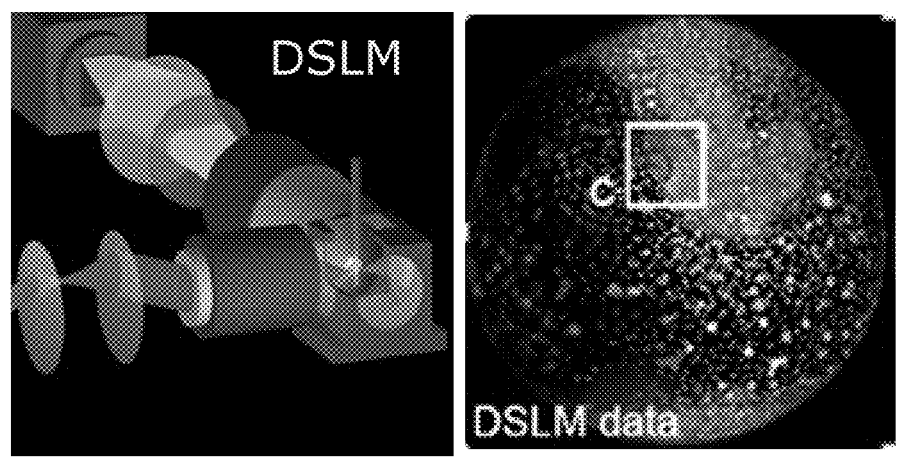
Figure 1E:
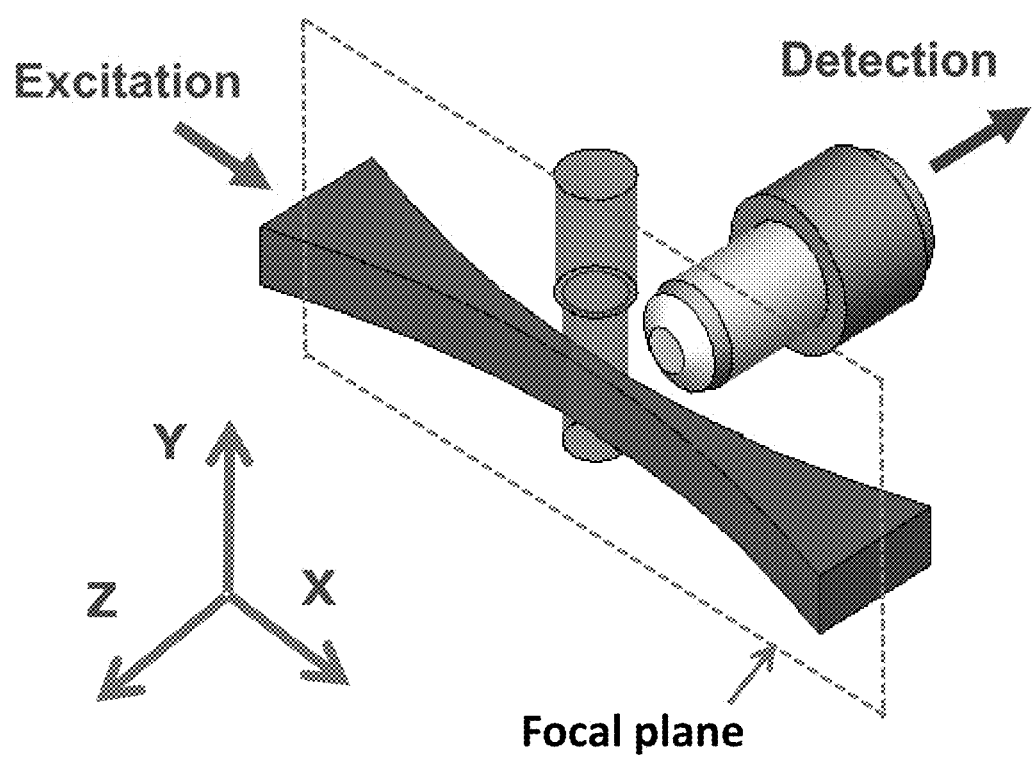
Figure 2A:
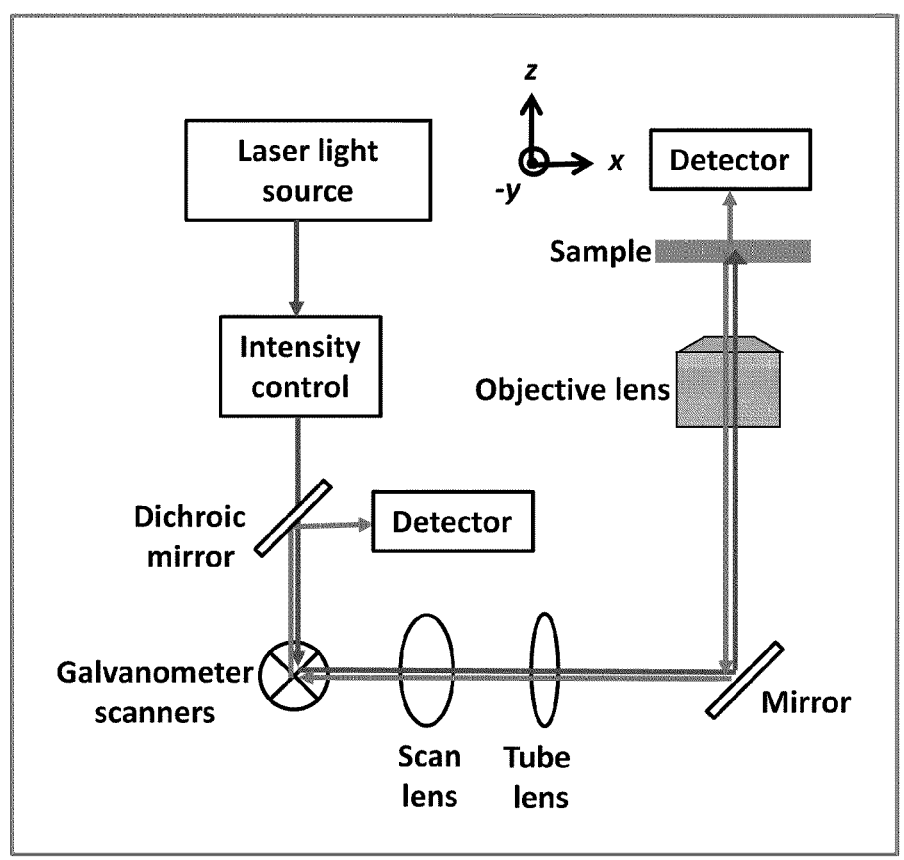
FIG. 2A provides a schematic of a conventional RAPS microscope.

Raster point scanning microscopy (RAPS), also known as laser scanning microscopy (LSM), is the standard way to collect 3-dimensional (3D) images of biological samples. As shown in FIG. 2A, which shows a simplified schematic of a conventional RAPS microscope, in RAPS the illumination light is shined onto the sample from above or below the sample, focused into a point by an objective lens, and detection of emitted light is done in the reflected or transmitted directions, collinear with the illumination direction. To obtain a 3D image, XY-coverage of the sample is done by raster-scanning the point across the sample, while Z-coverage is done by moving the focused point to a different plane, and raster-scanning is repeated. Z-sectioning is achieved by use of a pinhole in the detection, or by localizing the excitation in space via nonlinear optical processes such as two-photon absorption. RAPS microscopy is ideally suited for samples that are flat, and there are many widely-available commercial RAPS microscopes (such as from Zeiss), and many biological and medical laboratories have these instruments. It should be understood that any of these conventional RAPS microscopes may be incorporated into the device of the current invention.

LISH Microscopy

Figure 2B:
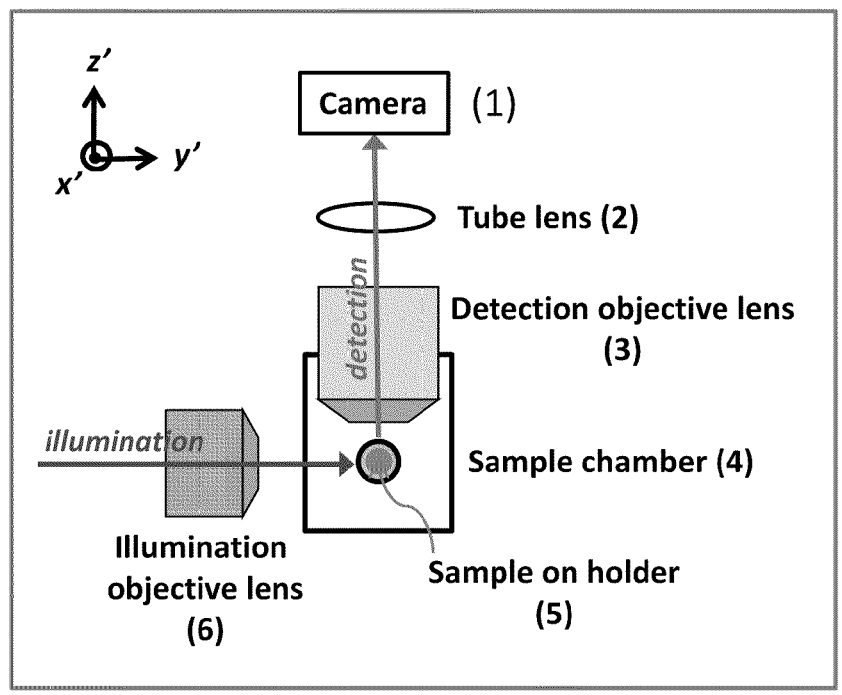
FIGS. 2B and 2C provide schematics of a conventional LISH microscope, with 2B providing a top view and 2C providing a 3D perspective view.
Figure 2C:
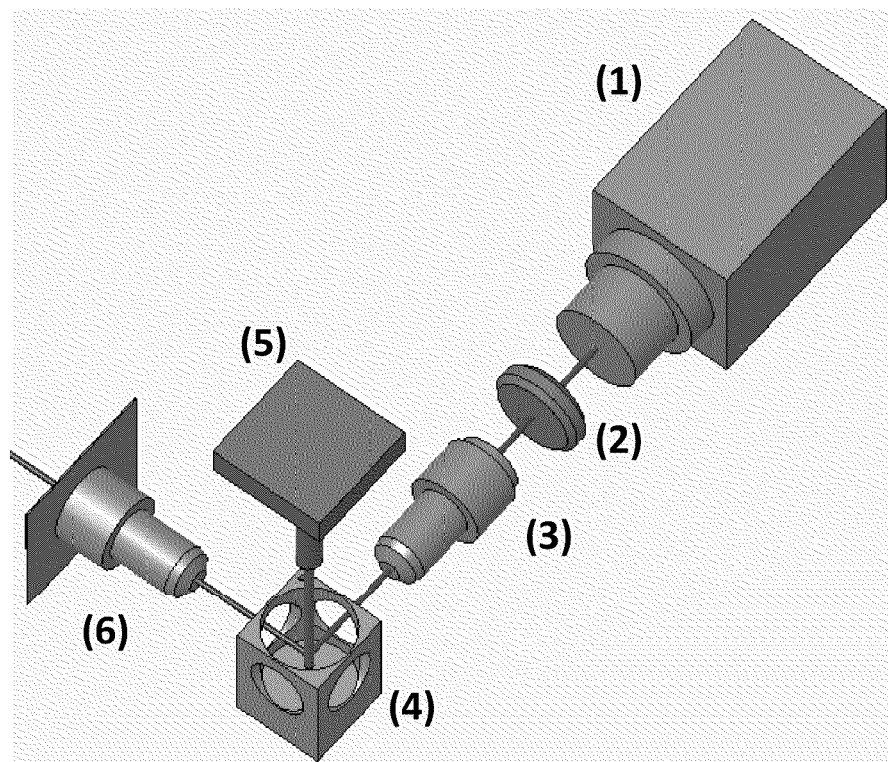

A schematic of a conventional LISH microscope is provided in FIG. 2B, with a 3d perspective view given in FIG. 2C. The basic LISH apparatus, as shown, includes an illumination objective (6) positioned along a first axis of a sample chamber (4). The sample chamber houses the sample to be imaged, which is attached to a holder and controller (5), preferably allowing control in x, y, z, and theta (rotational). A detection objective (3), a tube lens (2), and imaging device, such as, for example, a camera (1) are positioned in line of sight to the first illumination axis. Black solid lines depict the optical axis of the illumination and detection beams, going through (6) and (3), respectively. Not shown are the mechanical supports of the system. (For a detailed description of a LISH microscope, see, US Pat. Pub. No. 2009/0225413, the disclosure of which is incorporated herein by reference.)

As shown in the above schematic, LISH is a microscopy technique where the illumination is done from the side of the sample, creating a diffraction-limited planar sheet of light going across the sample. (See, J. Huisken and D. Y. R. Stainier, *Development* 136, 1963-1975 (2009), the disclosure of which is incorporated herein by reference.) Detection of the emitted light is done at 90 degrees from the illumination direction, orthogonal to the light sheet. Z-sectioning is achieved since only one diffraction-limited plane is illuminated at a time. The sample may be scanned through the plane (or inversely the plane could be scanned through the sample) to allow coverage of the whole sample volume.

LISH microscopy differs from RAPS microscopy in the geometry of the illumination and detection optical pathways. RAPS microscopy, which is a widely used imaging technology, uses a collinear (parallel or anti-parallel) geometry between the illumination and detection pathways. (See, e.g., Pawley, *Handbook of Confocal Microscopy*, 3$^{rd}$ Edition, New York: Springer (2006), the disclosure of which is incorporated herein by reference.) This results in some inherent advantages for LISH microscopy. In particular, because of the orthogonal geometry between the illumination and detection directions, the lateral extent of the illumination focus (together with the detection optics) determines the axial resolution of the final image. Compare this with conventional RAPS, where the final axial resolution is determined by the axial extent of the illumination focus. Since for a given focusing NA, the focus spot is always smaller laterally than axially, LISH needs to employ a substantially smaller focusing NA than conventional RAPS to reach the same axial resolution, which carries important implications, as will be discussed in detail later. In addition, particularly for imaging 3D biological samples, illumination in LISH is limited only to the plane that is being imaged, hence reducing photobleaching and phototoxicity; detection is done in parallel for the whole plane, usually with a CCD camera, hence time acquisition is fast, usually about 10-20 times faster than the RAPS technique.

Because of these inherent advantages, conventional LISH has been the subject of intensive study, and the literature discloses many recent implementations of the conventional LISH technique. (See Huisken and Stainier, referenced above.) Some of these techniques include Orthogonal Plane Fluorescence Optical Sectioning (OPFOS), Selective Plane Illumination Microscopy (SPIM), Ultramicroscopy, Digital Scanned Laser Light Sheet Fluorescence Microscopy (DSLM), etc. Although these different implementations have different specialized features, they have one common critical feature: the illumination is done with a sheet of light orthogonal to the detection direction. In the DSLM technique, the light sheet is synthesized by scanning, via a movable device such as a galvanometer mirror, a low-NA focused beam of light. Seen from the side through the detection objective, the focused beam of light appears as a line of light. At any time instant the sample is illuminated by only a line of illumination, which when summed over the scanned space and over time, yields an illuminated light sheet.

Inventive RAPS/LISH Microscopy

The current invention describes an imaging apparatus that can operate in both RAPS and LISH modes. As each imaging modality (RAPS or LISH) is ideally suited for a different kind of sample, a biomedical research laboratory would ideally like to have access to both types of microscopy, allowing access to the widest possible selection of samples. However, there is a lack of commercially available LISH microscopes, and even if a commercial LISH microscope is available there is the high cost, both in monetary and space-related terms, associated with owning two different microscopes in order to do both LISH and RAPS microscopy.

The current invention specifically deals with using a novel optical arrangement to allow for the coexistence of the LISH and RAPS modes of operation in the same imaging instrument. An embodiment of the combined RAPS/LISH microscope is shown schematically in FIG. 3A (top view) and FIG. 3B (3D perspective view). As seen, the imaging instrument consists of a RAPS module (inside dotted box labeled (I) in FIG. 3A), an optical relay (inside dotted box labeled (II)), and a LISH module (inside dotted box labeled (III)). The optical relay allows routing of the illumination laser light to either the RAPS module or LISH module, therefore allowing sharing of any parts of microscope that are optically upstream of it for both the operation of RAPS and LISH. Specifically, the laser light sources, laser light intensity control, galvanometer scanners, and scan optics could be shared for the two modules, bringing down the cost and complexity of the imaging instrument (as compared to 2 separate instruments that perform RAPS and LISH microscopy separately).

The RAPS module could be of any standard design, examples of which can be easily found since there are many already commercialized implementations. Note that FIG. 3A shows an instance of RAPS in the inverted geometry, other geometries (such as upright) could be equally used in our invention.

The optical relay ((II) in FIG. 3A) could be of many designs, as will be discussed further below, but with the same goal to allow routing of the illumination laser light to either the RAPS or the LISH module. One specific implementation, as shown in FIG. 3, uses a system of lenses to relay the image of the scanned laser spot that is at the back focal plane of the RAPS objective lens (10) to the back focal plane of the LISH objective lens (6).

Figure 3A:
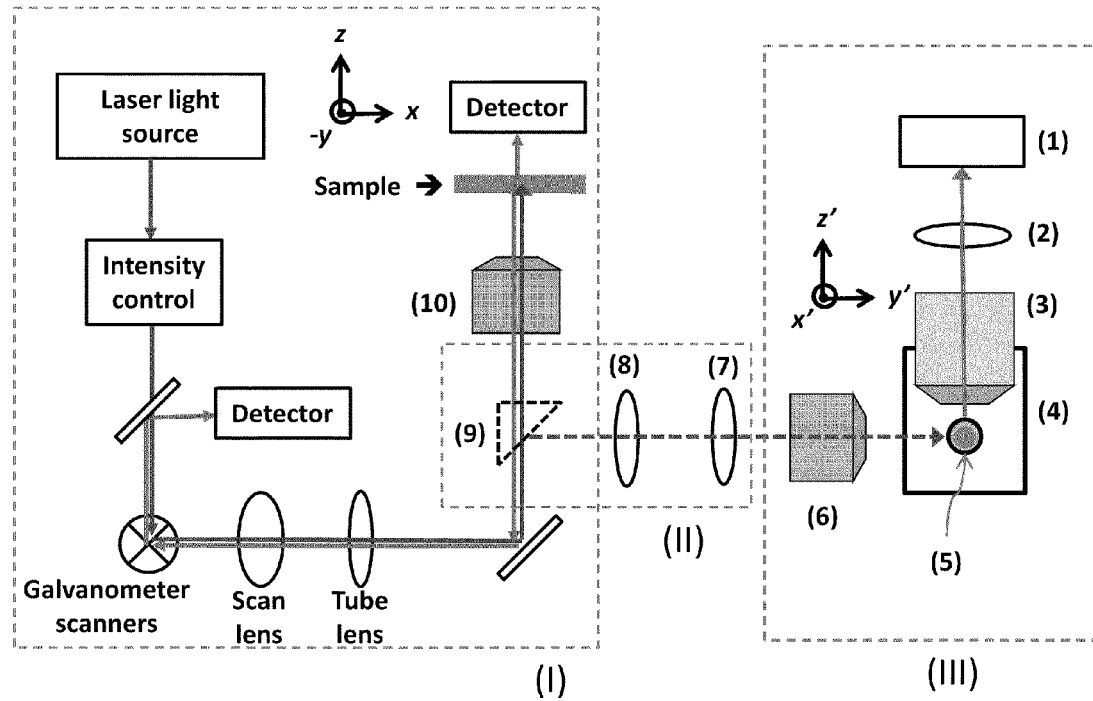
FIGS. 3A and 3B provide schematics of a microscope device in accordance with the current invention that allows for the operation of the device in both RAPS and LISH modes, where 3A provides the top view schematic, with three dotted boxes labeled (I), (II), and (III), representing the RAPS, optical relay, and LISH modules, respectively, and 3B provides a 3D perspective view of the optical relay and LISH module of the setup.

The LISH module ((III) in FIG. 3A) of the combined RAPS/LISH microscope consists of essentially the basic LISH microscope described in FIG. 2B. At a minimum, the LISH module consists of: an illumination objective lens (6), sample changer (4), sample holder and x-y-z theta controller (5), detection objective lens (3), tube lens (2), cameras (1), and computer control (not shown). Turning to the individual components of the LISH unit:

- (6): LISH illumination objective lens. This is the optical component that takes in the scanned laser light coming from the main RAPS microscope and produces a planar light sheet, along the x'y' plane, at the sample position. For the basic design, a standard microscopic objective could be used. Different, more specialized optical components and/or combinations could be used here to create the light sheet at the sample, e.g. cylindrical lenses, axiconic lenses (to create Bessel beams), etc. Some of these alternatives will be described in greater detail in the alternative embodiments below.
- (4): Sample chamber. This is made of a suitable material and design for the sample and the imaging application. For example, if the sample needs to be in water, then (4) has to be water-tight, with optical access windows. If water-immersion objectives are to be used, then appropriate water-sealing features have to be implemented. Sample chambers suitable for LISH microscopy have been described in the literature. (See Huisken, J. & Stainier, D. Y. R., *Development* 136, 1963-1975 (2009), the disclosure of which are incorporated herein by reference.)
- (5): Sample holder and controller. Similar to the sample chamber, these should be made of a suitable material and design for the sample and the imaging application, and have been described in the literature. For example, for imaging of live fruit fly embryos, the embryos could be affixed with glue to a small (diameter ~1 mm) capillary tube, which is held vertically by a pipette holder, which in turn is held by a combination of motorized stages that allow control of the samples x-y-z positions and rotation around the x' axis. Although so far only biological samples have been discussed, it should be understood that the same imaging instrument could be applied to image non-biological samples.
- (3): Detection objective lens for LISH. This is the optical component through which the signals are collected. Its optical axis is parallel to the z' direction, hence is orthogonal to the light sheet created by the illumination objective. For samples that have to be in an aqueous medium, a water-dipping objective should be used here. For certain appropriate applications, objectives (6) and (3) could be gel-coupled to the sample. Both the illumination and detection objectives should be mounted on appropriate stages with adjustable x, y, z, tip, tilt, roll (or any subset of these), to facilitate confocal orthogonal alignment of the two objectives at the sample area. It could also be useful to mount the detection objective on motorized stage that can be moved along its optical axis (the z' direction).
- (2): Tube lens. This lens focuses the infinity-corrected light from the detection objective lens at the camera, creating an image of the sample focal plane at the camera.

(1): Detector. The image created at the sample by the light sheet is captured by the detector. In choosing a suitable detector for LIS microscopy, close attention should be paid to make sure the specifications of the detector (frame rate, quantum yield, read noise, etc.) match those required by the imaging applications. Depending on the wavelength of the emission light that is being recorded, appropriate optical fillers should be placed before the camera to allow only the right wavelengths to pass through. Emissions of different wavelengths could also be separated and recorded separately with multiple cameras, using any of the many widely known optical spectral separation techniques. It should be understood that the emitted light detected may include, but not be limited to, fluorescence, scattered excitation light, and Raman-shifted scattered light The combined microscope includes one or more laser light sources, to be shared with between the RAPS and LISH imaging modes. Although any light source suitable for exciting a sample in both RAPS and LISH modes may be used, in a preferred embodiment the device incorporates at least one continuous-wave laser with wavelength in the visible range (approximately 400-700 nanometers), and at least one pulsed laser with wavelengths in the near-infrared (NIR) range (approximately 700-1400 nanometers). The pulse duration of the pulsed-laser could be in the nanosecond, picoseconds, or femtosecond range. The continuous-wave laser light source(s) would produce one-photon-excited signal contrast, such as, but not limited to, one-photon-excited fluorescence, Rayleigh scattering, Raman-shifted scattering. The pulsed light source(s) would produce multi-photon-excited signal contrast, such as, but not limited to, two-photon-excited fluorescence, second harmonic generation, sum frequency generation, stimulated Raman scattering, third harmonic generation.

To allow the excitation source to operate in both RAPS and LISH modes, the excitation source must be coaxial with the RAPS illumination/detector objective (10). Accordingly, in one embodiment the excitation source enters through the RAPS illumination/detector objective (10). (Although, FIG. 3 shows an embodiment with a geometry designed for an inverted RAPS microscope with the light entering along the +z direction, an equivalent setup could be applied to an upright RAPS microscope, however, in such a case, the scanned laser light enters from the top, along the −z direction, and (9) would oriented so that it still directs light towards the +x direction.)

Although many different types of objective lenses and excitation sources may be used, at a minimum this objective must be chosen such that RAPS microscopy can be carried out. Accordingly, in a preferred embodiment the RAPS illumination/detector objective (10) is a spherical lens that allows for the light source to be scanned, via suitable scanning optics, such as, for example, galvanometer scanners, along a desired axis such that a planar excitation light sheet may be produced. (A detailed description of this scanned light source, and its optical advantages, will be described below.)

Figure 4:
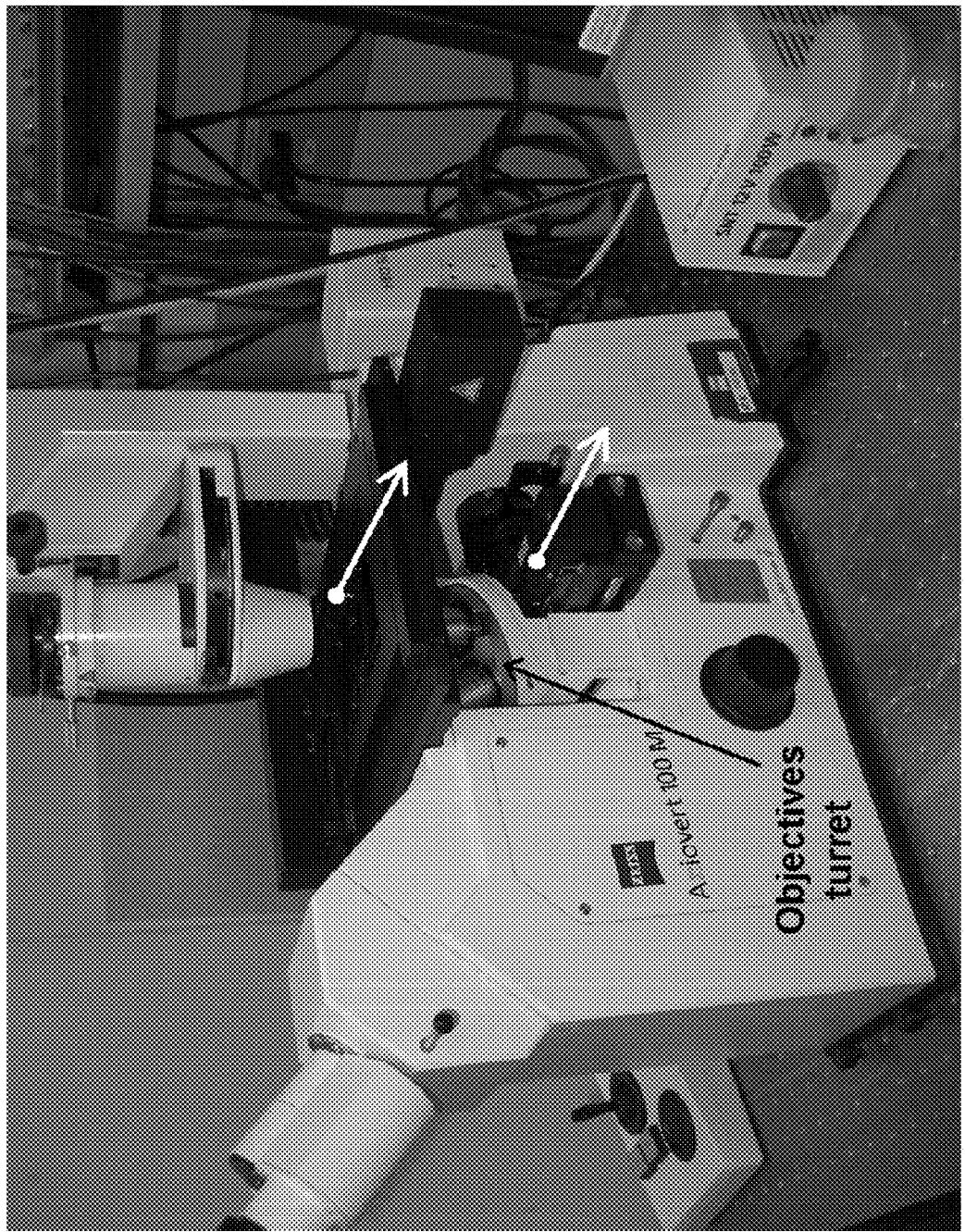
FIG. 4 provides an image of two possible optical positions for integrating an optical relay with an RAPS microscope in accordance with the current invention.

Regardless of the RAPS illumination/detection optics, a reflecting mirror (9) is disposed in the path of the illumination beam to direct the illumination from the excitation source to the LISH module (in the current embodiment, sideways from the +z to the +x direction). It should be understood that although mirror (9) is shown below (10), it could also be placed above (10) (essentially anywhere after the tube lens of the RAPS microscope), depending on the available physical access of the RAPS module. (FIG. 4 shows these two possible locations in relation to a standard RAPS microscope, see white arrows.) If the device of the current invention is to be incorporated into a conventional RAPS microscope, it will be understood that certain modifications may be required. For example, the sample stage normally used for RAPS might have to be removed to allow room for (9) and the redirected laser beam, while if (9) is placed above (10), then objective (10) is removed for operation of the LISH module.

In order to allow the LISH and RAPS modules of the imaging instrument to use the same laser excitation source lenses (8) and (7) are provided to optically relay the back focal plane of the RAPS objective lens (10), to the back focal plane of the LISH objective lens (6). In combination, these lenses operate as an optical relay. There is significant flexibility in designing the lens system for the optical relay. In the simplest possible design the lenses are provided in a 4f configuration, where (8) and (7) are focusing lenses of equal focal length f, placed so that (8) is a distance f away from (10), (7) is 2f away from (8), and (6) is f away from (7). Using such an arrangement will allow for the scanned laser beam at the back focal plane of (10) to be imaged onto the back focal plane of (6) with a 1:1 magnification.

Again, although a simple 4f configuration may be used, if more space is needed between the LISH module and the RAPS microscope, or for increase flexibility in the design and operation of the combined microscope system, the optical relay could be extended by adding more lenses; for example, a second identical set of lenses to (8) and (7) will turn the 4f system into an 8f system, and so on. Alternatively, lenses of different focal lengths could be used to provide magnification ratios different than 1:1. The critical requirement of the optical relay system is that the back focal plane of (10) is imaged onto the back focal plane of (6).

Figure 3B:
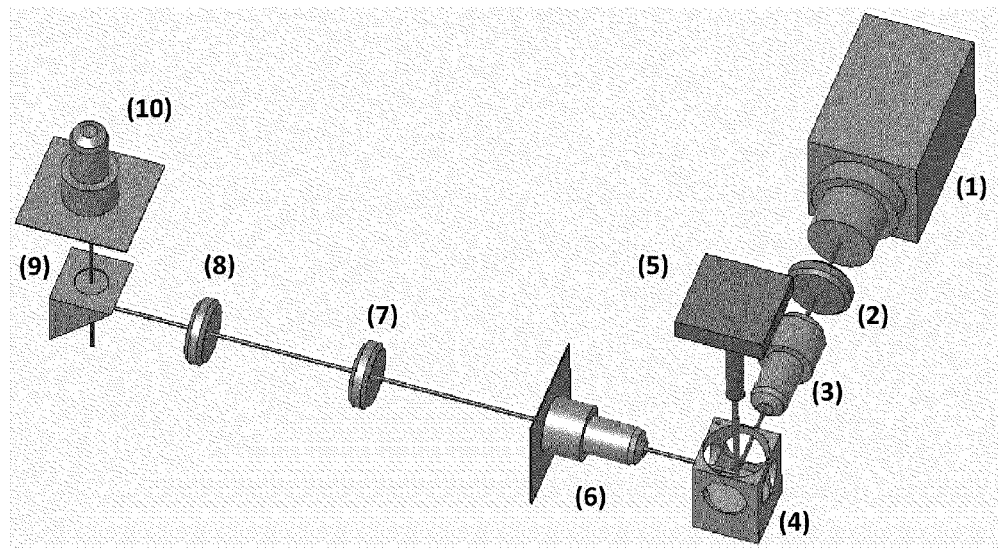

While in the embodiment shown in FIG. 3A-B, the back focal plane of (6) is vertical, along the x'z' plane, with additional lenses and routing mirrors, the back focal plane of (6) could be designed to be in any arbitrary orientation in space. Also, while the embodiment shown in FIG. 3A-B, the illumination light sheet is along the x'y' plane, it can designed (with additional lenses and routing mirrors, and/or with control of the galvanometer scanners) to be in any arbitrary orientation in space. In those cases, the detection arm of the LISH module ((3), (2) and (1)) has to be changed accordingly, ensuring that their optical axis is always orthogonal to the light sheet. The LISH module could also be straightforwardly designed so that the orientations of the back focal plane of (6) and the light sheet could be adjustable, facilitating optimized imaging of different kinds of samples. As mentioned, components (9), (8), and (7) (and all additional lenses and routing mirrors if the optical relay is extended further than depicted) comprise the optical relay. This combination of optical elements could also be referred to as a periscope. In designing the mechanical support of this optical relay, not shown in FIG. 3, attention should be paid to make the system robust, free from mechanical perturbations, and easy to attach/detach, as this is the step involved in switching between the RAPS and LISH modes of operation. One possible design for the periscope is to have components (9), (8), and (7) mounted inside a mechanical housing which could be reproducibly mounted to or demounted from the RAPS microscope, thus allowing switching between the two modes of operation. Another possible design is to have (9) alone mounted in a movable mechanical housing (eg a filter-cube slider mount), while (8) and (7) are housed in a separate, non-moving housing, so that (9) could be reproducibly moved in and out of the optical pathway for switching between the RAPS and LISH modes.

It should be understood that although the combined LISH/RAPS microscope could be engineered from scratch to coexist with the RAPS module within the same imaging instrument, the LISH module could also be added to an existing RAPS microscope (commercial or home-built). The same novel optical relay device may be used to allow for the coexistence of the two RAPS and LISH modules in a newly-designed imaging instrument In incorporating the inventive optical system with a commercially available laser scanning microscope, the optical relay described above, such as, for example, a 4f-lens system, to transfer the image of the scanned laser beam, normally at the back focal plane of the objective used for RAPS, to a new location, enabling the addition of an LISH module. Once this reconfiguration is completed, the LISH and RAPS modules can be operated independent from each other, and switching between the two modes of operation involve only mechanically removing/installing the RAPS objective and optical relay (or parts of it). These different configurations will be described in greater detail below.

LISH Module as Add-on to Existing Raps Microscope

As mentioned above, the LISH module could be constructed as an add-on to an existing RAPS microscope. The RAPS could be either a commercial or home-built system. In such an embodiment, the operation of the LISH module is quite independent of the RAPS. The optical relay (periscope) is the only component that links the RAPS microscope to the LISH module. As described in previous sections, in such an embodiment the optical relay could be readily designed so that it, or part of it, could be mounted/demounted in a reproducible manner, with minimal impact to the optical alignment of the whole system, allowing for convenient switching between the RAPS and LISH modes of imaging. Although exemplary embodiments of the device have been described above, it should be understood that both upright and inverted microscopes could be modified/designed as described above to add the LISH capability to standard RAPS capability.

LISH Module as Built-in Feature of Raps Microscope

The LISH and RAPS modules could be engineered from scratch to coexist in a laser scanning microscope. The same basic design of the optical relay, as described above, is used to allow switching between the two modes of operation. Note that the optical relay, with as many optical relay stages as necessary, allows the LISH module to be physically apart from the RAPS module. This allows utilization, with minimal modifications, of existing designs of single-mode RAPS or LISH microscopes in constructing the dual-mode instrument.

Note that regardless of whether the LISH module is designed as an add-on or an integral component from scratch, the two modules share the same galvanometer scanners, so the place where the optical pathway is switched between the two modules, i.e. where the optical relay begins, could be any place after the scanners and the scanning optics. One possible convenient location for the periscope to take out the scanned light is before the objective turret, in the space normally occupied by the filter cubes for wide-field fluorescence, as shown in FIG. 4. Switching between the two modes would involve moving a slider-like module to redirect the light. In addition, it should be noted that the optical relay, or part of it, is the only part of the LISH module that needs to be moved for switching between the two imaging modes. The rest of the LISH module, being physically away from the main RAPS microscope body, could be positioned in any convenient location.

Operation of the Combined LISH/RAPS Microscope

Operation of the RAPS Module

When the instrument is used in RAPS mode, the optical relay, or part of it, is taken out of the optical path. Thus the LISH module is optically isolated from the RAPS microscope. Operation of the RAPS module may then proceeds as with any standard RAPS microscope.

Operation of the LISH Module:

To use the instrument in LISH mode, the optical relay is place into the optical path of the instrument, so that mirror (9) is in the optical pathway to direct the beam from the z direction to the x direction. Thus the illumination light is directed towards the LISH module. If mirror (9) is designed to be above (10), then (10) has to be removed for LISH operation. Additionally, the sample stage of the RAPS microscope might have to be removed to make room for installation of the optical relay, as described above.

Using the software that controls the RAPS microscope, the illumination laser is raster-scanned along the x direction in the back focal plane of (10). This line scan of the illumination light travels through the optical relay, creates a line scan along the x' direction in the back focal plane of (6), goes through objective (6), and creates a planar sheet of light along the plane x'y' at the sample in chamber (4). The emission of the sample generated by the illumination light sheet is then imaged onto the camera (1) through the detection objective (3) and tube lens (2).

Sample controller (5) is used to rotate and move the sample in the 3 dimensions x', y', and z'. Movement of the sample could be coordinated with camera image capture via computer control to obtain images of different sections of the sample. For example, to get a rectangular volumetric image of the sample, the sample is moved in steps along the z' direction, with the camera capturing an image after each step. Another way to do volume scan is to do an area scan in xy at the back focal plane of (10), which translates to an area scan in x'z' in the back focal plane of (6), which in turn yields a volume scan at the sample with sequential x'y' planes. The detection objective (3) would then have to be moved in synchrony with the sequential x'y' planes to ensure that each plane remains in focus at the camera.

For more automated operation, the computer control of the operation of the LISH module could be coordinated with the control of the main RAPS microscope. Alternatively, software control of the whole system could be designed so that the LISH operation is integrated into the normal operation of the RAPS module.

Additional Features

Although, the above describes the basic optical arrangement of the invention, it should be understood that other features maybe added to this basic design. In particular, the infinity optical space within the optical relay (between elements (9) and (8) and between (7) and (6) in the above embodiment) provides a convenient space for addition of different optional components (see below) to add features to the LISH module.

Additional features for the LISH module include (but are not restricted to): multi-photon excitation, shutter to control illumination, bidirectional illumination, multi-angle illumination, bidirectional detection, structured illumination, cylindrical illumination lenses, headstage with eyepieces for direct viewing, detection optical filters, spectral separation of the emitted light (via dichroic beamsplitters and bandpass filters) to allow simultaneous detection of different wavelengths, anisotropic. Several of these key features are described below.

Multi-Photon Excitation

The literature discloses a technique that reduces the detrimental effect of scattering/refraction to imaging: multiphoton (MP) excitation. In standard single photon (SP) excitation, one photon of the illumination light interacts with the sample and gives rise to an emitted photon (usually in the form of fluorescence). In MP excitation, the excitation step involves n number of photons, where n is equal to or greater than 2. The multiple number of photons interact with the sample essentially simultaneously, and then give rise to emitted radiation, which could be in the form of fluorescence, second harmonic generation, third harmonic generation, etc. (See, J. Pawley, *Handbook of Confocal Microscopy*, $3^{rd}$ Edition, New York: Springer (2006), the disclosure of which is incorporated herein by reference.) For MP excitation, the excitation probability, and hence the emitted signal, is proportional to $I\hat{\ }n$, where I is the instantaneous intensity of the laser light at the sample. This can be contrasted with the SP case, discussed above, where the signal is proportional to I.

In carrying out the MP excitation, any suitable source of excitation energy may be utilized, however, in a preferred embodiment pulsed lasers are used in order to achieve the high instantaneous intensities required to produce significant levels of emitted signals (which are proportional to $I\hat{\ }n$ for MP excitation processes). The pulsed lasers can be of any suitable type, such as, for example, nanosecond, picosecond, or femtosecond-duration pukes. The shorter the puke, the lower the total laser energy is needed to achieve the same level of instantaneous intensity. In light of this, for biological samples, in order to minimize thermal damage, femtosecond pukes (with duration of hundreds of femtosecond or shorter) are preferred. In turn, picosecond and nanosecond pulses might be more appropriate for non-biological samples, where thermal damage is less of a concern.

Scanned Light Sheet

Although a static light sheet may be used with the LISH module of the current invention, by utilizing a cylindrical lens and appropriate apertures in the optical relay, (see, J. Huisken & D. Y. R. Stainier, *Development* 136, 1963-1975 (2009), the disclosure of which is incorporated herein by reference.) in the preferred embodiment the illumination light sheet is created by the fast lateral scanning along a plane direction of the spherically-focused laser light (i.e., the y axis), generating a scanned sheet along a second plane (i.e., the xy-plane, perpendicularly to the z detection axis). (See, Keller, P. J., et al., (2008), cited above.)

A scanned light sheet can be generated by fast scanning of the beam, with a period of 1 ms to cover the full field of view (FOV). This kHz-speed is fast enough to produce an effectively uniform illumination intensity across the y-extent of the FOV, for imaging exposure times of tens of ms or more. For shorter exposure times, faster scanning hardware could be employed (e.g. resonant scanners or spinning polygon mirrors can scan in the range of 10-100 kHz). In this embodiment, the lateral extent of the illumination focus spot determines the thickness of the scanned light sheet, while the confocal parameter of the focal region (the distance over which the lateral extent remains less than two times its smallest value) determines the imaging field of view.

The scanned sheet feature provides dramatic and unexpected improvements in imaging capabilities over the conventional static sheet, which is typically produced by focusing through a cylindrical lens. In short, the implementation of the light sheet via fast scanning of a spherically-focused light beam achieves higher excitation power throughput, better light spatial uniformity along the vertical dimension of the FOV, and allowing convenient execution of non-coherent structured illumination to improve signal contrast. (See, Keller, P. J., (2008); and Keller, P. J. et al., *Nat. Methods* 7, 637-(2010), the disclosures of each of which are incorporated herein by reference.) In addition, it has been recently demonstrated that the scanned light sheet minimizes scattering artifacts compared to the static light sheet illumination used in SPIM. (See, Fahrbach, F. O., et al., cited below.) For multi-photon-excited signal contrast, the scanned sheet, with its instantaneous line illumination providing an additional dimension in focusing as compared to a static sheet, yields higher illumination intensity and hence higher signal levels (for the same total illumination light power).

Bidirectional Illumination

To increase the field of view of LISH, the illumination may be done from opposite sides of the sample. A schematic of an LISH apparatus including a bidirectional light source is provided in FIG. 5. As shown, in this embodiment, the illumination beams from the +x and −x directions are adjusted so that their fields of view slightly overlap at the center of the sample, effectively doubling the final field of view. (See, Huisken, J. & Stainier, D. Y. R., *Opt. Lett.* 32, 2608-2610 (2007), the disclosure of which is incorporated herein by reference.) With an optical setup like in FIG. 5, or any other that is optically equivalent, sequential illumination from opposite directions of the sample is achieved by controlling the shutters, preferably through computer control and coordinated with camera image capturing. Sequential bidirectional illumination helps to create a larger and more uniform illumination area at the sample, and bidirectional excitation is particularly preferred for multi-photon application, because in the case of MP-LISH, because the signal is spatially confined due to its $I\hat{\ }n$ dependence, the illumination from opposite could be done concurrently, saving in time acquisition and complexity of data acquisition controls. The resulting image would then have about twice the field of view, with the same resolution and contrast as illuminated from one side at a time.

Figure 5:
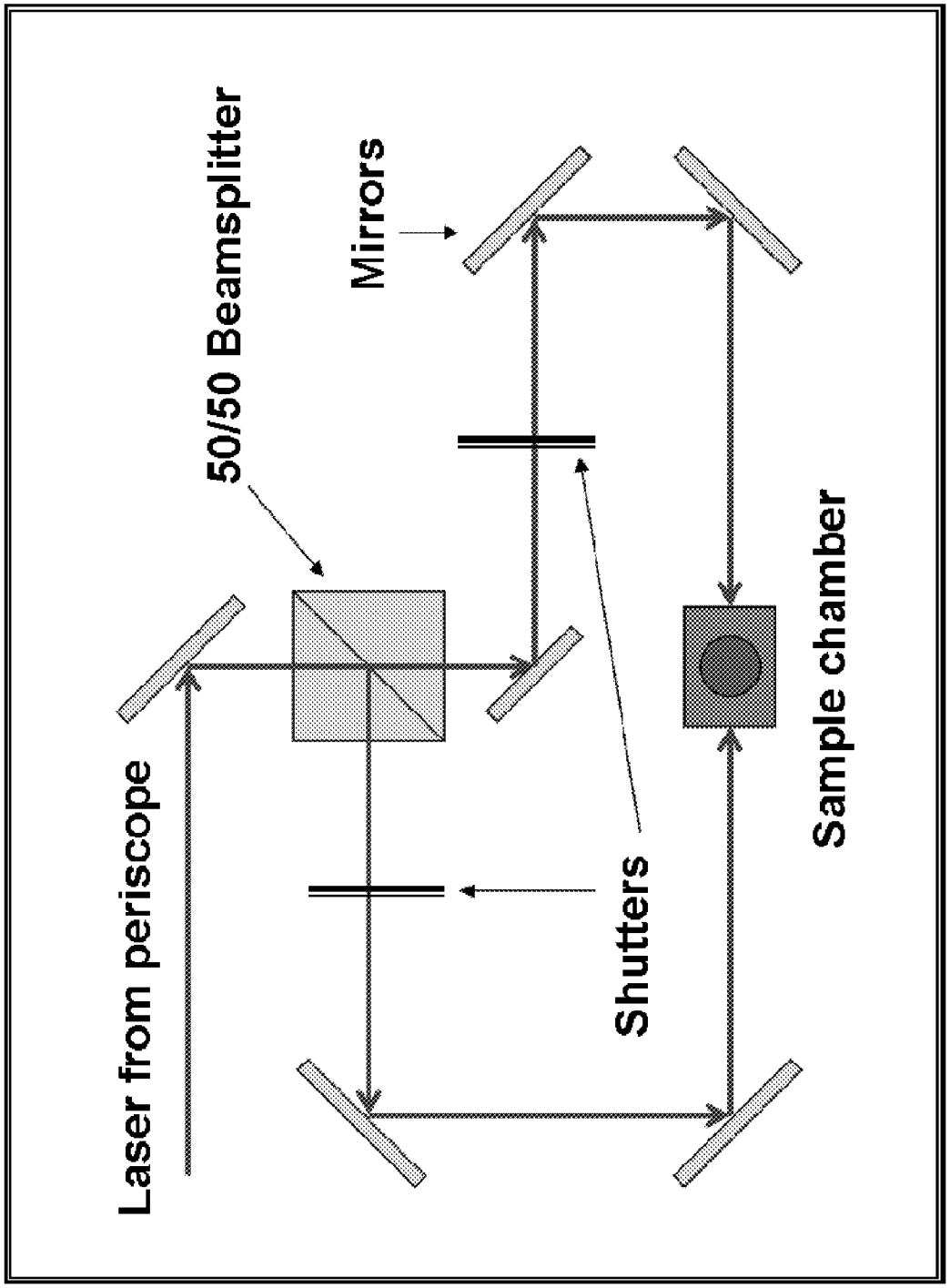
FIG. 5 provides a schematic of an optical setup allowing for bidirectional illumination of the sample in accordance with the current invention.

The key design points of the setup in FIG. 5 is the use of (i) a beamsplitter, and (ii) shutters to produce sequential illumination from opposite directions. Opening/closing of shutters do not affect the propagation direction of optical beams, thus ensuring optimal alignment. One type of beamsplitter that could be used is the broadband (or for whichever appropriate illumination wavelength), non-polarizing type. Another type of beamsplitter that could be used is the polarizing type, in which case a means to rotate the polarization of input laser beam (e.g. a hall-wave plate), not shown in FIG. 5, is needed before the beamsplitter.

Adjustable Illumination NA:

The ability to adjust the NA of the illumination may be used to provide greater flexibility for the imaging device, since the signal depends quite sensitively to the NA, as described above. One way to achieve this is to have the illumination light go through a beam expander with adjustable expanding ratio, which then yields an adjustable illumination beam diameter, which in turns allow for fine-tuning the illumination NA.

Focal Volume Engineering:

Taking into consideration that in LISH microscopy (MP or SP), the lateral resolution of the captured image is determined by the detection optics, independent of the illumination NA; and for MP, the signal is proportional to $I\hat{\ }n$, it would be possible to engineer the spatial extent of the focal volume of the illumination light so that it is optimized for a particular sample.

For example, an anisotropic NA could be used for the illumination to obtain more uniform signal profile in a scattering sample, effectively increasing the depth penetration. For instance, for a particular sample, a particular NA_z is used along the z-axis for the excitation, to meet whatever specification for axial resolution that is needed. If sheet illumination is used the NA along the x-direction would be NA_x 0, and if standard line illumination is used NA_x=NA_z. Because of the scattering in the sample, and assuming that the center of the focal volume is significantly inside the sample, the light intensity has decreased significantly at the focal center, decreasing the signal contrast and thus also the excitation depth penetration.

This scenario can be mitigated by using NA_x>NA_z. The stronger lateral focusing takes light energy away from the right side part of the sample, where the illumination first penetrates the sample, and put it more to the left towards the focal center, increasing the signal contrast in this deeper region, hence improving the signal uniformity over the entire sample and increasing the depth penetration. The larger NA_x illuminates more of the sample laterally away from the focal center, but does not degrade the detected lateral resolution, since that is solely determined by the detection optics. And, by increasing only NA_x, leaving NA_z unchanged, in trying to get more signal at the larger depth, the optimal axial (z) resolution may be maintained.

Anisotropic NA could also be done with NA_x<NA_z, to have less peak excitation intensity, to reduce supra-quadratic photodamage. In general, lower NA_x reduces supra-quadratic photodamage, but increases total light energy imparted onto sample (i.e. increases linear 1 photon photodamage) and reduces signal rate as described earlier.

It will be understood that the above described anisotropic illumination NA could be produced by in any suitable way, such as, for example, two sequential, adjustable slit apertures, oriented 90 degree to each other; and beam expanders that expand each dimension independently, using cylindrical lenses. Another implementation of focal volume engineering could use a Bessel beam. The benefit of a Bessel beam compared to conventional Gaussian beam includes a larger field of view for the same sheet thickness at the center. Bessel beams would be of particular advantage for MP excitation, since the side lobes of a Bessel profile, normally a problem in imaging with 1p excitation, would produce significantly less signal because of the nonlinear dependence of the signal on the intensity. In yet another alternative, focal volume engineering could be implemented with spatial light modulators such as, for example, liquid crystal SLM, digital micromirror device (DMD), etc.

Exemplary Embodiments

The person skilled in the art will recognize that additional embodiments according to the invention are contemplated as being within the scope of the foregoing generic disclosure, and no disclaimer is in any way intended by the foregoing, non-limiting examples.

Figure 6:
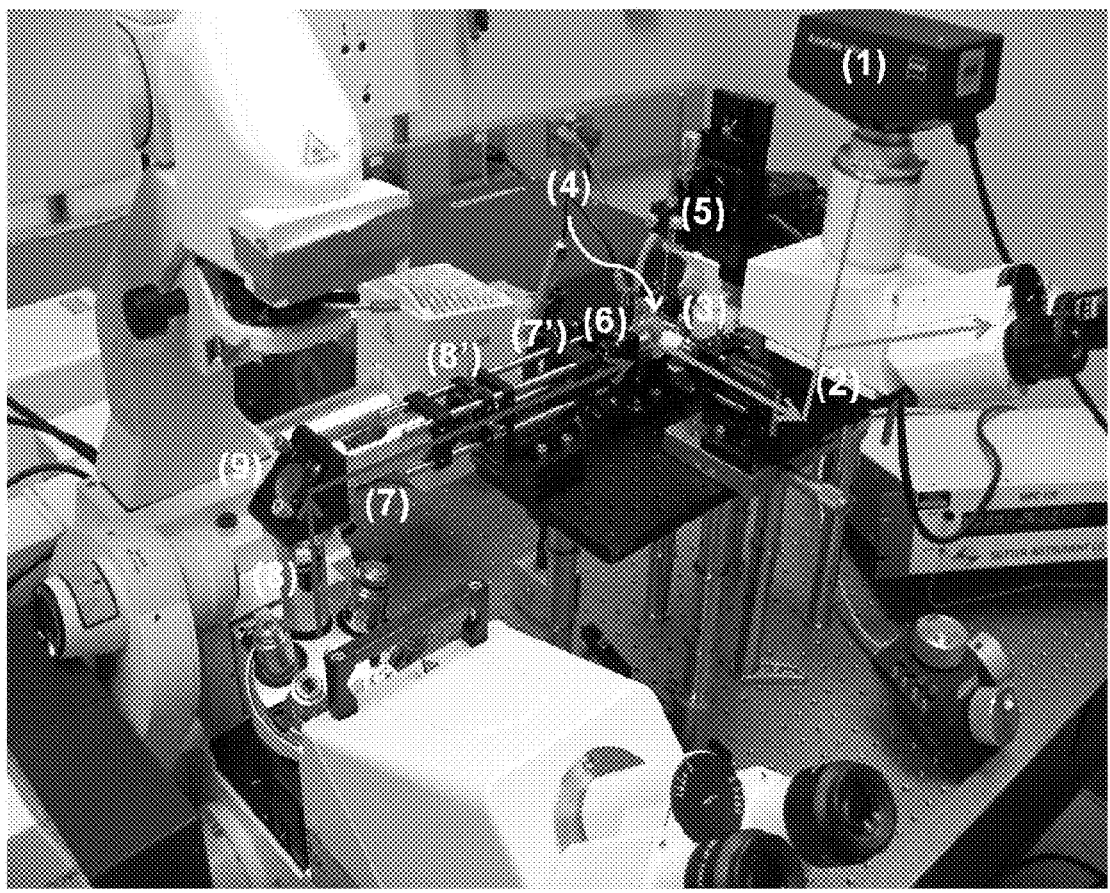
FIG. 6 provides a picture of an exemplary implementation of a dual-mode microscope in accordance with the current invention.

FIG. 6 shows the picture of an example of an implementation of the combined LISH/RAPS microscope of the current invention that allows for both LISh and RAPS microscopy. This implementation follows closely the schematic shown in FIG. 3A, and the components have been labeled with the same numbering convention for ease of comparison. The implementation in FIG. 6 adds a LISH module to an existing commercial RAPS microscope (Zeiss 510Inverted NLO). In the picture, the RAPS microscope can be seen on the left side, while the add-on LISH module is on the right side. Routing mirror (9) is put behind objective lens (10) (which has been removed and not seen) of the RAPS module. Lens (8) of the optical relay lies upstream of mirror (9), and the optical relay is of the 8f-design, where two pairs of lenses (8)&(7) and (8')&(7') are used to relay the scanned laser spot to the back focal plane of LISH illumination objective lens (6). The rest of the LISH module is similar to what is described in FIG. 3A, with the addition to the detection arm of a headstage with binoculars for direct eye viewing.

SUMMARY OF THE INVENTION

Accordingly, the dual-mode imaging microscope of the current invention allows for the execution of both LISH and RAPS imaging in a single instrument. This novel dual-mode device will allow researchers to have access to both types of microscopy, allowing access to the widest possible selection of samples. In addition, the device will reduce the high cost and space requirements associated with owning two different microscopes (LISH and RAPS).

Doctrine of Equivalents

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A dual-mode imaging microscope comprising:
an excitation source, said excitation source being capable of producing an excitation beam, and being disposed such that the excitation beam is directed along at least one excitation beam path, wherein the at least one excitation beam path is provided with a scanning optic capable of scanning said excitation beam in at least two dimensions;
a sample holder in optical communication with said excitation source such that a sample contained therein is excited by said excitation beam;
a light scanning microscope unit comprising:
  a light scanning microscope excitation optic capable of focusing the scanned excitation beam on the sample holder such that a sample within the sample holder is raster-scanned in a pre-determined path, and
  a light scanning microscope detector defining at least one light scanning detection focal plane and capable of detecting an excitation generated signal contrast from the sample within the sample holder, the light scanning microscope detector being disposed such that the axis of detection of the at least one light scanning detection focal plane is substantially parallel to the excitation beam path as it intersects the sample;
a light sheet microscope unit comprising;
  a light sheet microscope excitation optic capable of using the scanned excitation beam to produce a substantially two-dimensional sample excitation region having an effectively uniform excitation intensity which extends in the direction of an excitation axis of the excitation beam path and transversely thereto and intersects with at least a portion of the sample holder, and
  a light sheet microscope detector defining at least one light sheet detection focal plane and capable of detecting an excitation generated signal contrast from the sample excitation region, the light sheet microscope detector being disposed such that the axis of detection of the at least one light sheet detection focal plane is substantially orthogonal to the sample excitation region; and
  an optical relay disposed downstream of said scanning optic, said optical relay capable of being removably interposed into the excitation beam path, such that said excitation beam may be directed either toward the light scanning microscope excitation optic or the light sheet microscope excitation optic.

2. The microscope as claimed in claim 1, wherein the optical relay is a periscope having a 4f optical configuration.

3. The microscope as claimed in claim 1, wherein at least one excitation source is a continuous-wave laser producing an excitation beam in the visible wavelength range, said excitation source being capable of inducing 1-photon-exicted signal contrast for imaging, and wherein said signal contrast is proportional to $I^n$, where I is the instantaneous intensity of the excitation beam at the sample excitation region and n is the number of photons involved in the excitation, and where n is 1.

4. The microscope as claimed in claim 1, wherein the at least one excitation source is capable of producing an excitation beam of high enough intensity to induce sufficient levels of multi-photon excitation to produce signal contrast for imaging, and wherein said signal contrast is proportional to $I^n$, where I is the instantaneous intensity of the excitation beam at the sample excitation region and n is the number of photons involved in the multi-photon excitation, and where n is greater than 1.

5. The microscope as claimed in claim 1, wherein the excitation source is a pulsed near-infrared laser selected from the group consisting of lasers having pulse durations in the range of nanosecond, picoseconds, and femtosecond.

6. The microscope as claimed in claim 1, wherein the detected signal contrast is selected from the group consisting of 1-photon-excited fluorescence, Rayleigh scattering, Raman-shifted scattering, second harmonic generation, third harmonic generation, sum frequency generation, and stimulated Raman scattering.

7. The microscope as claimed in claim 1, wherein the at least one excitation source is capable of creating two coaxial and oppositely aligned excitation beams, such that said sample excitation region is formed from the overlap of said two excitation beams.

8. The microscope as claimed in claim 1, wherein the numerical aperture of at least one of either the light scanning microscope excitation optic or the light sheet microscope excitation optic is adjustable.

9. The microscope as claimed in claim 8, wherein the adjustable numerical aperture comprises a beam expander with an adjustable expanding ratio.

10. The microscope as claimed in claim 1, wherein the numerical aperture of at least one of either the light scanning microscope excitation optic or the light sheet microscope excitation optic is anisotropic along at least two axes of said excitation beam.

11. The microscope as claimed in claim 1, wherein focal volume engineering is applied to the excitation beam to optimize for light sheet imaging.

12. The microscope as claimed in claim 11, wherein focal volume engineering is implemented using one of the techniques selected from the group consisting of having the numerical aperture of the excitation focusing optics being anisotropic along at least two axes of said excitation beam, and having the excitation beam be a Bessel beam.

13. The microscope as claimed in claim 11, wherein the focal engineering is implemented by one or more optical elements selected from the group consisting of two orthogonally oriented sequential adjustable slit apertures, a plurality of independently expanding beam expanders, liquid crystal spatial light modulators, digital micromirror device spatial light modulators, and axiconic lens.

14. The microscope as claimed in claim 1, wherein the sample holder is moveable relative to the sample excitation region along or about at least one axis.

15. The microscope as claimed in claim 1, wherein the sample excitation region is moveable relative to the sample holder along or about at least one axis.

16. The microscope as claimed in claim 1, wherein the excitation beam is one of either substantially planar-shaped or linearly-shaped.

17. The microscope as claimed in claim 1, wherein the light sheet microscope unit incorporates a technique selected from the group consisting of Orthogonal Plane Fluorescence Optical Sectioning (OPFOS), Selective Plane Illumination Microscopy (SPIM), Ultramicroscopy, and Digital Scanned Laser Light Sheet Fluorescence Microscopy (DSLM).

18. A method of imaging an object using a dual-mode imaging microscope comprising:
producing an excitation beam, and directing said excitation beam along an excitation beam path;
scanning said excitation beam along a predetermined path;
placing a sample within the optical path of said excitation beam to generate a signal contrast;
directing said excitation beam into an optical relay capable of selecting between one of either a light scanning mode or a light sheet mode;
wherein in the light scanning mode, the method further comprises:
focusing the scanned excitation beam to a point scanning region such that the sample is raster-scanned by the excitation beam to produce a signal contrast in said sample, and
detecting said signal contrast along a detection axis that is substantially parallel to the excitation beam; and
wherein in the light sheet mode, the method further comprises:
focusing said scanned excitation beam to produce a substantially two-dimensional sample excitation region having an effectively uniform excitation intensity which extends in the direction of an excitation axis of the excitation beam path and transversely thereto and intersects with at least a portion of the sample holder, and
detecting said signal contrast along a detection axis that is substantially orthogonal to the sample excitation region.

19. The method as claimed in claim 18, wherein the optical relay is a periscope having a 4f optical configuration.

20. The method as claimed in claim 18, wherein at least one excitation beam is produced with a continuous-wave laser producing an excitation beam in the visible wavelength range, said excitation source being capable of inducing 1-photon-exicted signal contrast for imaging, and wherein said signal contrast is proportional to $I^n$, where I is the instantaneous intensity of the excitation beam at the sample excitation region and n is the number of photons involved in the excitation, and where n is 1.

21. The method as claimed in claim 18, wherein the at least one excitation beam is of high enough intensity to induce sufficient levels of multi-photon excitation to produce signal contrast for imaging, and wherein said signal contrast is proportional to $I^n$, where I is the instantaneous intensity of the excitation beam at the sample excitation region and n is the number of photons involved in the multi-photon excitation, and where n is greater than 1.

22. The method as claimed in claim 18, wherein the excitation beam is produced via a pulsed near-infrared laser selected from the group consisting of lasers having pulse durations in the range of nanosecond, picoseconds, and femtosecond.

23. The method as claimed in claim 18, wherein detecting the signal contrast includes using a detection technique selected from the group consisting of fluorescence, second harmonic generation, third harmonic generation, sum frequency generation, and stimulated Raman scattering.

24. The method as claimed in claim 18, further comprising forming at least two coaxial and oppositely aligned excitation beams, such that said sample excitation region is formed from the overlap of said two excitation beams.

25. The method as claimed in claim 18, wherein the focusing of the excitation beam further includes adjusting the numerical aperture of a focusing optic.

26. The method as claimed in claim 18, wherein the focusing of the excitation beam further includes anisotropically adjusting the numerical aperture of a focusing optic such that the excitation beam is anisotropic along at least two axes.

27. The method as claimed in claim 18, wherein the imaging is performed in one of either a 3D or 4D mode.

* * * * *

UNITED STATES PATENT AND TRADEMARK OFFICE
CERTIFICATE OF CORRECTION

PATENT NO. : 8,570,649 B2
APPLICATION NO. : 12/916124
DATED : October 29, 2013
INVENTOR(S) : Thai V. Truong et al.

Page 1 of 1

It is certified that error appears in the above-identified patent and that said Letters Patent is hereby corrected as shown below:

In the Specification

The Statement of Federal Funding should read "This invention was made with government support under Grant No. EY018241 and Grant No. HG004071 awarded by the National Institutes of Health and under Grant No. DBI0852883 awarded by the National Science Foundation. The government has certain rights in the invention.".

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*